United States Patent [19]
Bull

[11] Patent Number: 6,098,451
[45] Date of Patent: *Aug. 8, 2000

[54] METHOD AND APPARATUS FOR RAPID DETERMINATION OF BLOOD SEDIMENTATION RATE

[76] Inventor: Brian S. Bull, 2526 Loma Linda University Medical Center, Loma Linda, Calif. 92350

[ * ] Notice: This patent is subject to a terminal disclaimer.

[21] Appl. No.: 09/201,321

[22] Filed: Nov. 30, 1998

Related U.S. Application Data

[60] Continuation of application No. 08/901,593, Jul. 28, 1997, Pat. No. 5,844,128, which is a division of application No. 08/718,632, Sep. 17, 1996, Pat. No. 5,986,461, which is a division of application No. 08/270,681, Jul. 12, 1994, Pat. No. 5,594,164.

[51] Int. Cl.[7] .................................................. G01N 33/49
[52] U.S. Cl. ............................................................ 73/61.66
[58] Field of Search ................................ 73/61.63–61.67, 73/864.91, 61.66; 422/102; 356/39

[56] References Cited

U.S. PATENT DOCUMENTS

| | | | |
|---|---|---|---|
| 3,914,985 | 10/1975 | Von Behrens | 73/61.66 |
| 4,091,659 | 5/1978 | Massey, III et al. | 73/61.66 |
| 4,701,305 | 10/1987 | Hattori et al. | |
| 5,594,164 | 1/1997 | Bull | 73/61.66 |
| 5,714,125 | 2/1998 | Sagstetter | 422/102 |

*Primary Examiner*—Robert Raevis
*Attorney, Agent, or Firm*—Flehr Hohbach Test Albritton & Herbert LLP

[57] ABSTRACT

An apparatus and method for rapid determination of erythrocyte sedimentation rates for a blood specimen (29) which can be linearly transposed to Westergren sedimentation rates. The method includes the steps of inducing accelerated rouleaux formation in the specimen (29) in an amount sufficient to begin settling at substantially the decantation rate for the specimen. In one embodiment a structure (27) which produces a very thin cross-sectional region (37) of the specimen (29) inside the lumen (23) of a specimen container (21) is provided to accelerate rouleaux formation. In an alternative embodiment (120), accelerated rouleaux formation is accomplished using a centrifuge (122). A third embodiment employs a movable rod (223) mounted inside the specimen tube (221) to induce accelerated rouleaux formation. All embodiments of the process next employ gravity settling the specimen in a near horizontal oriented container (21, 121, 221). Thereafter, the amount of settling occurring is determined. A sealed specimen container (21, 121, 221) which permits thorough mixing of blood in a very small diameter container for use in performing the method also is provided.

4 Claims, 9 Drawing Sheets

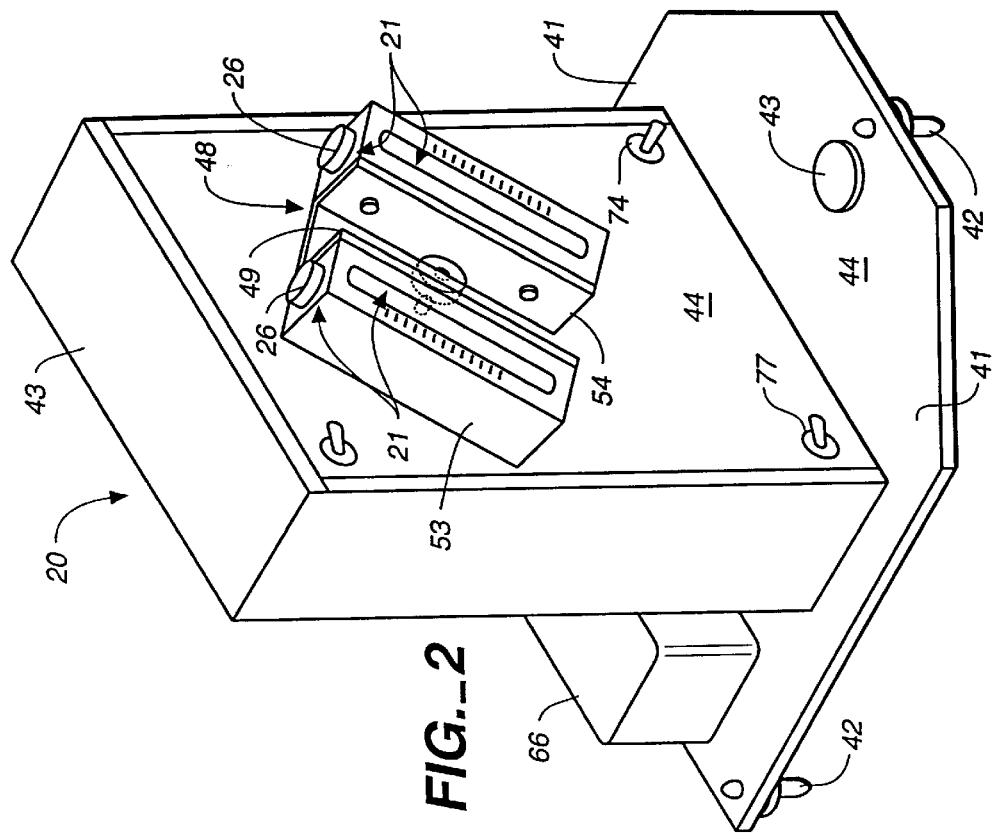
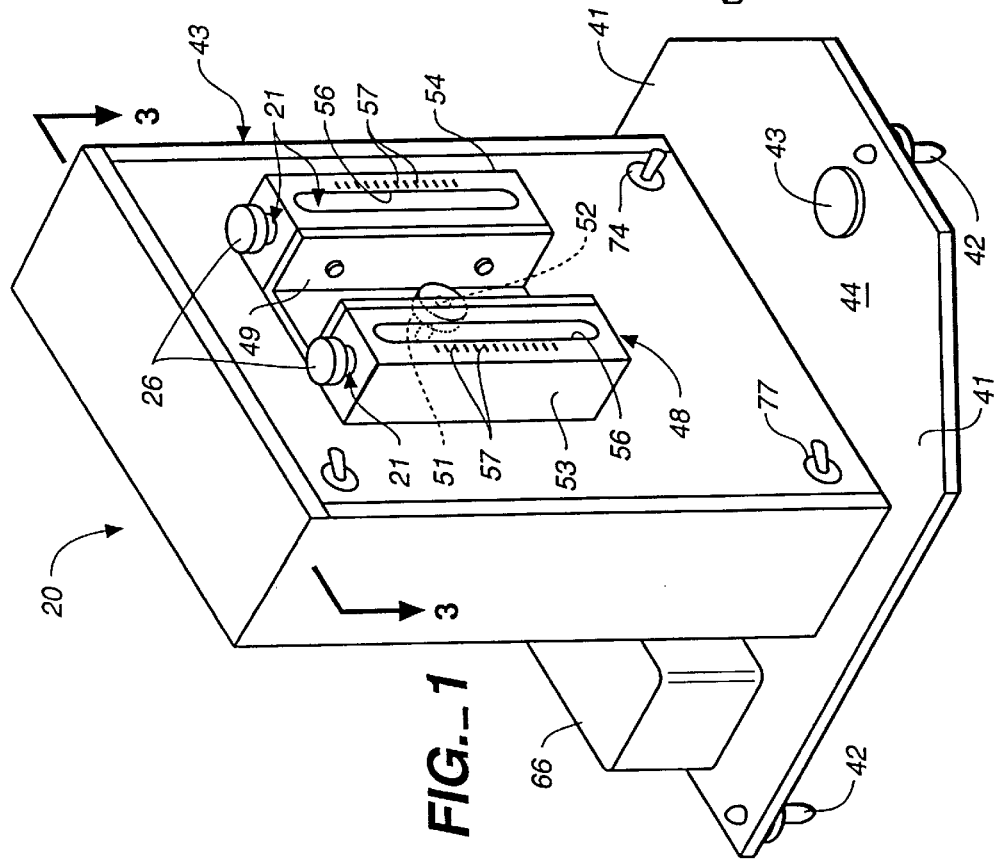

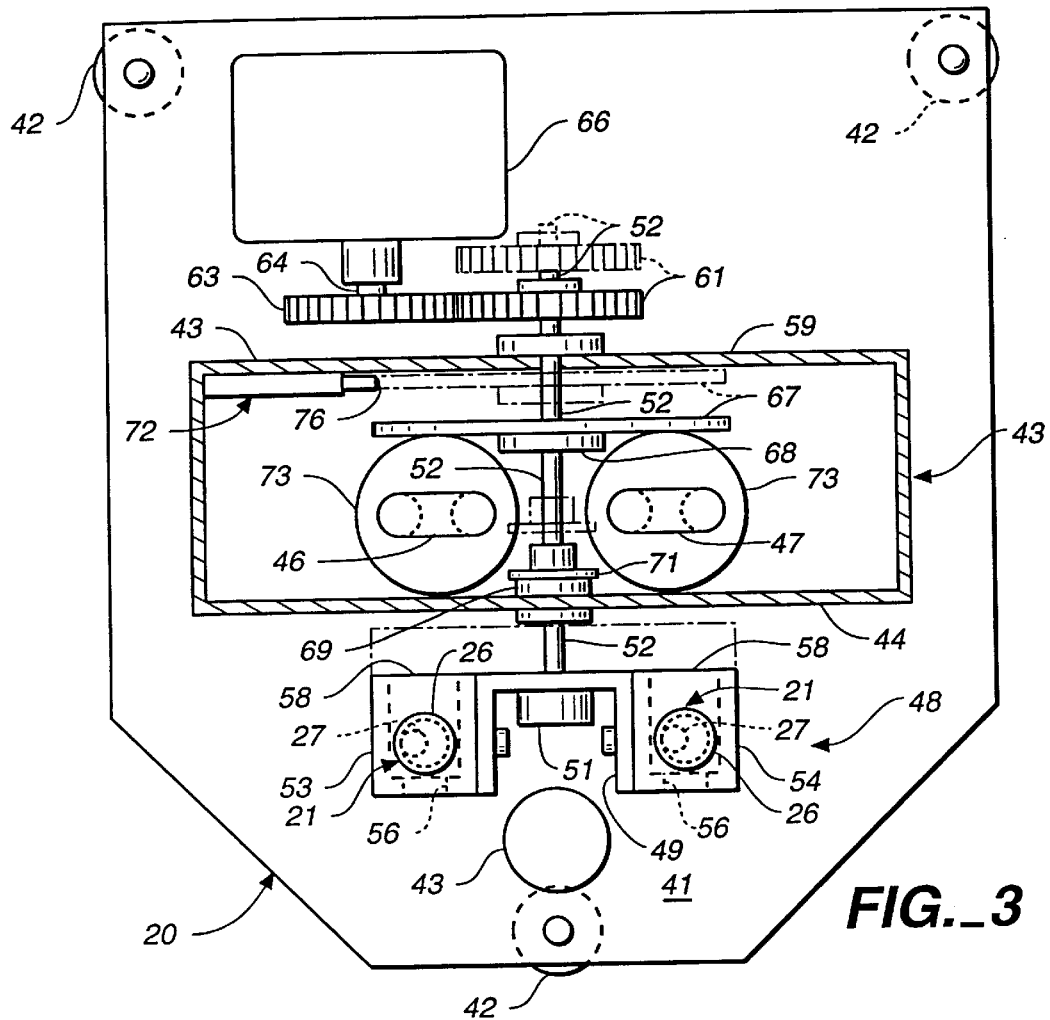
FIG._3
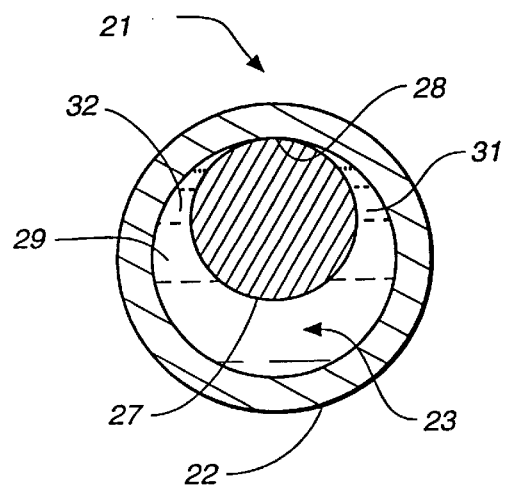
FIG._5

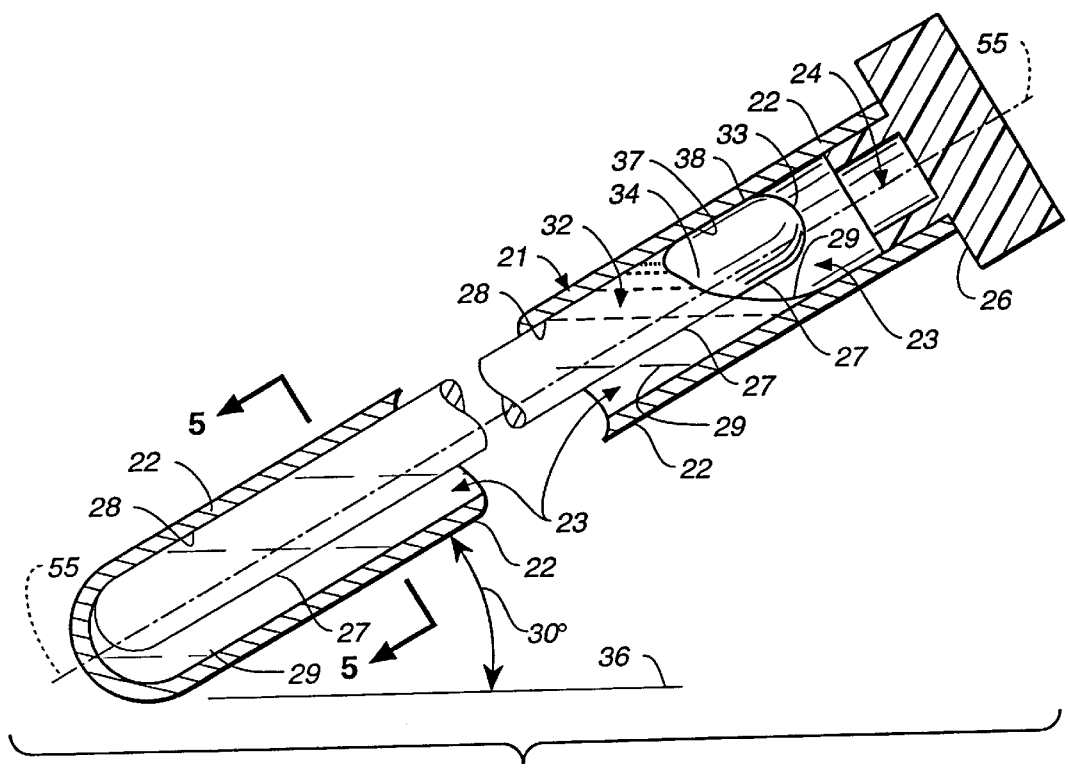
FIG._4
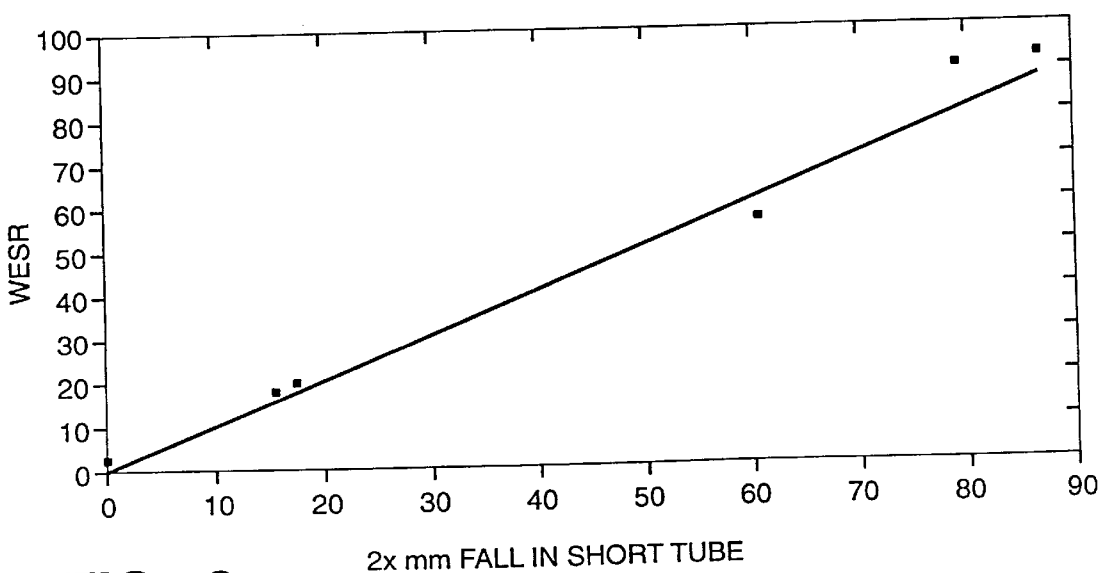
FIG._6

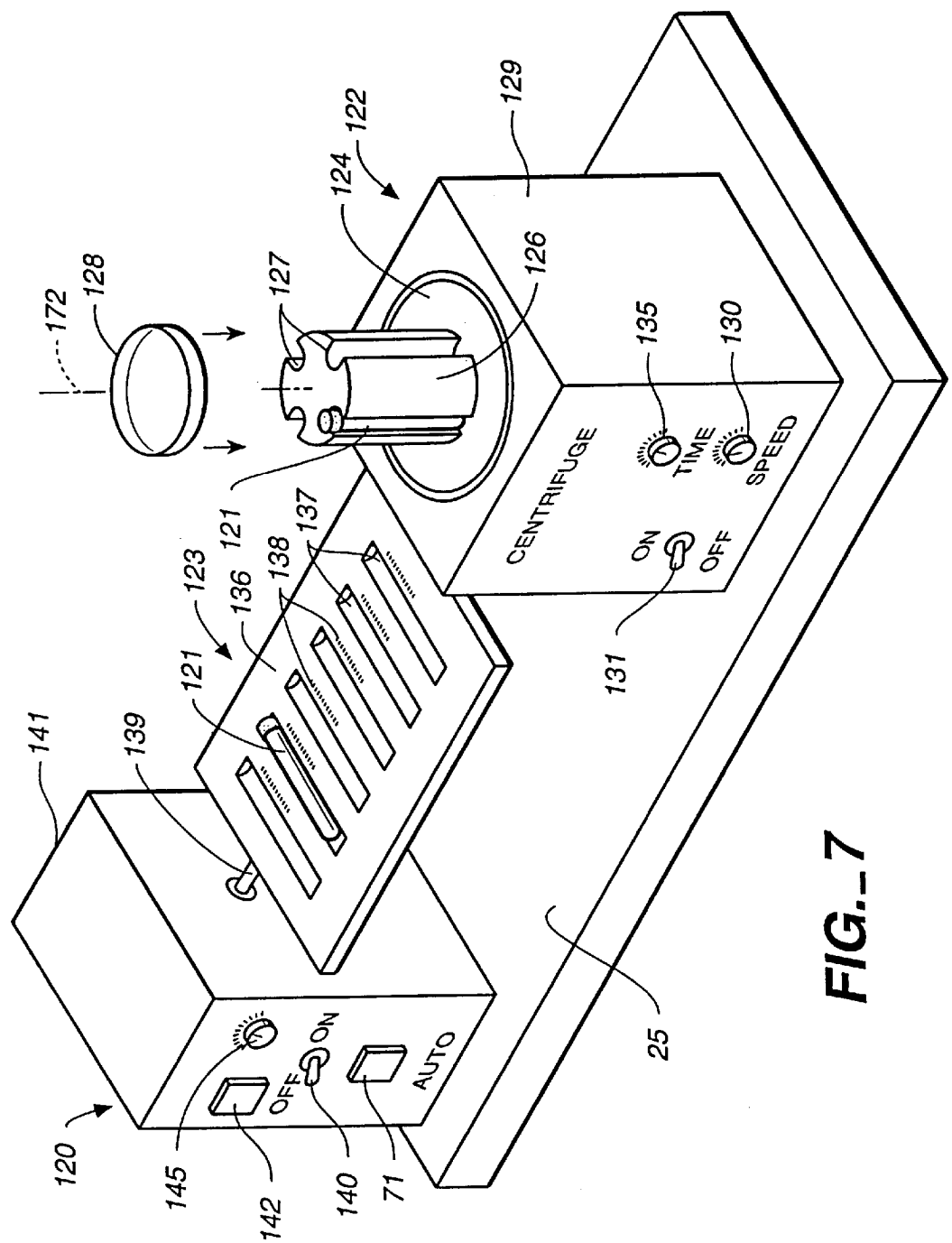
FIG._7

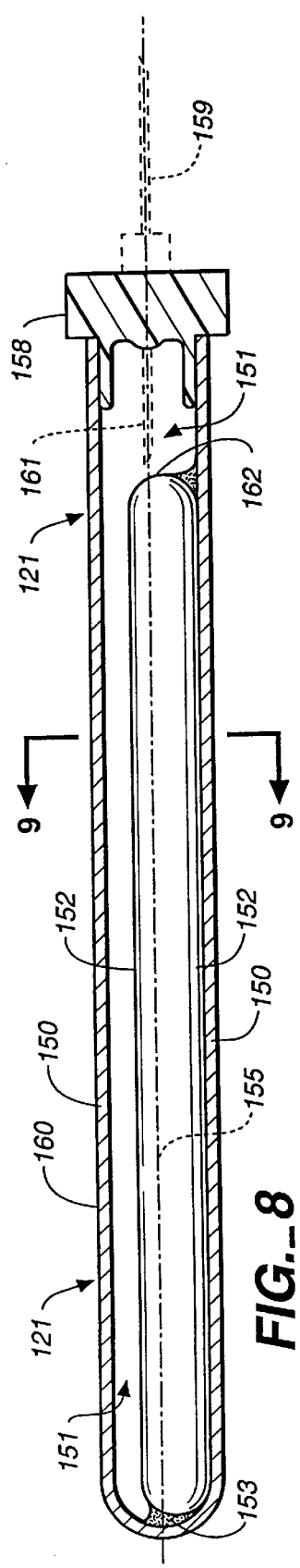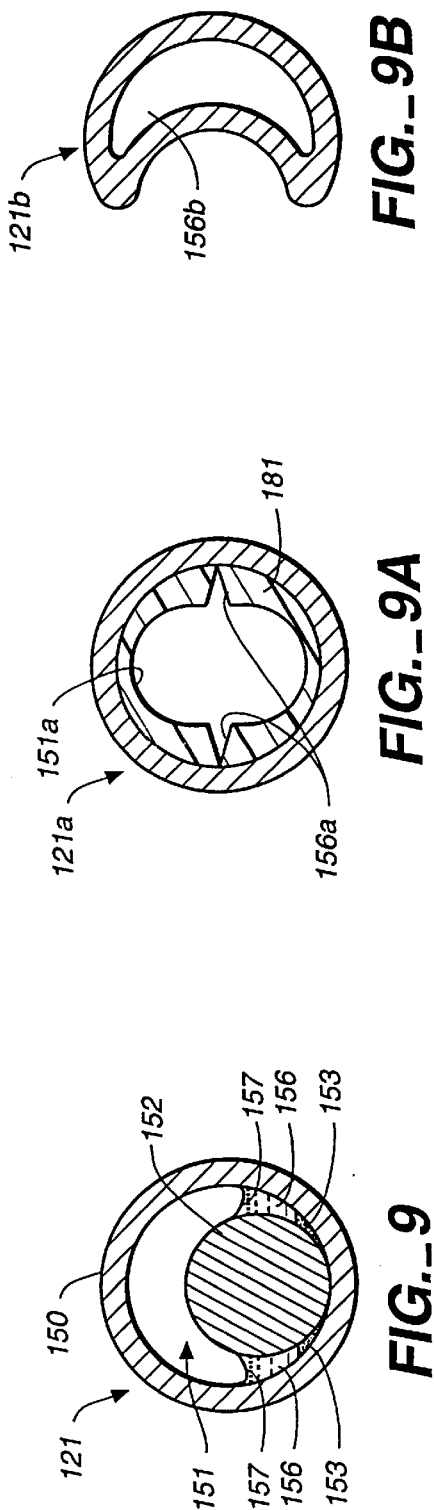

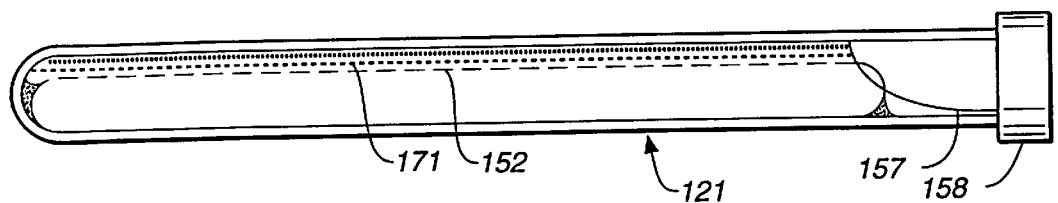
FIG._10
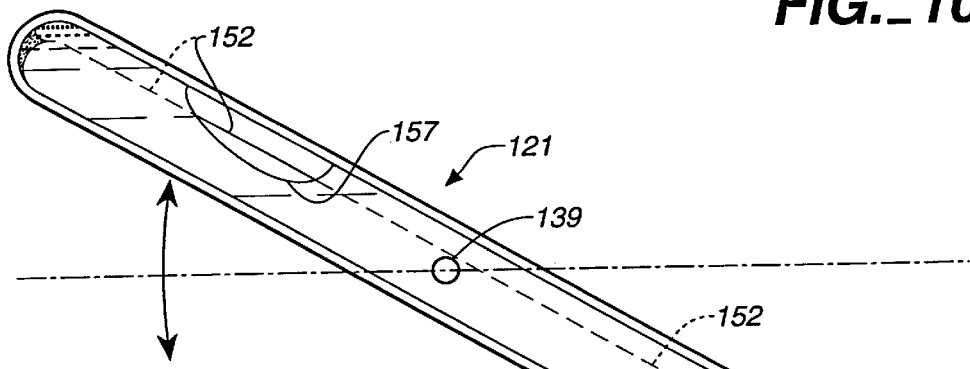
FIG._11
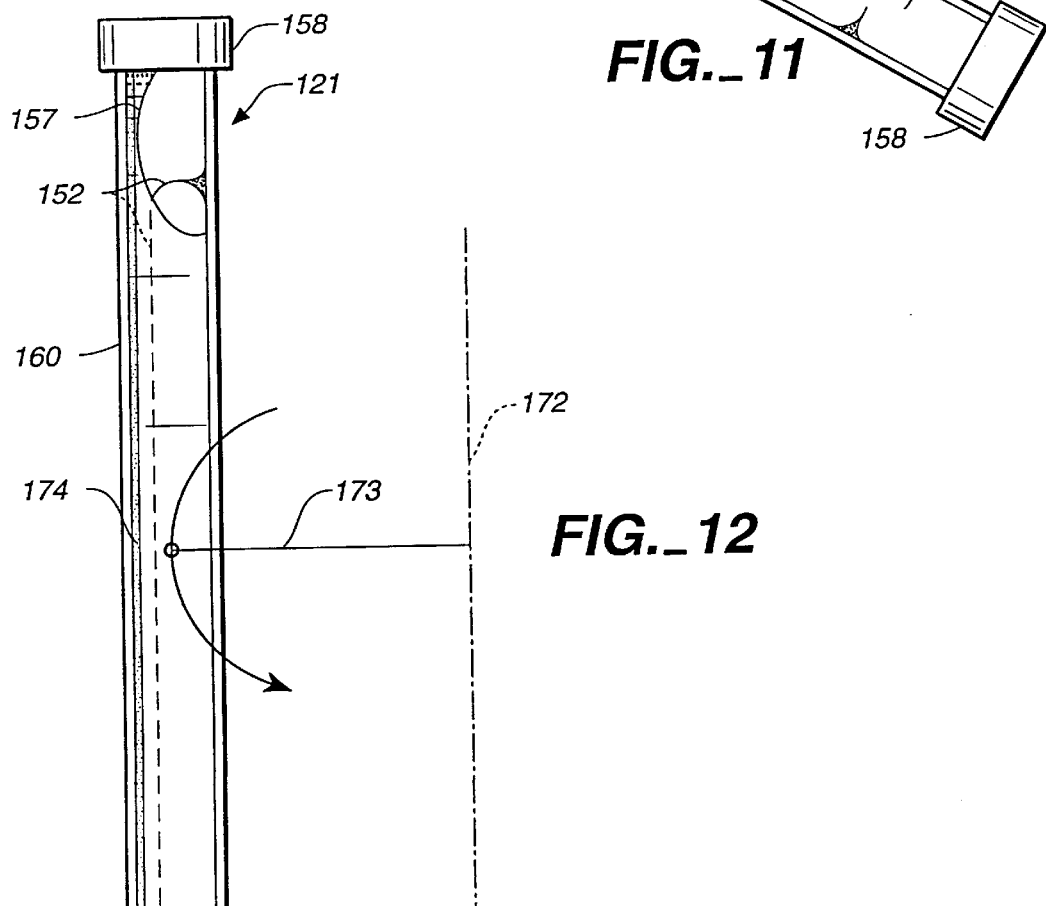
FIG._12

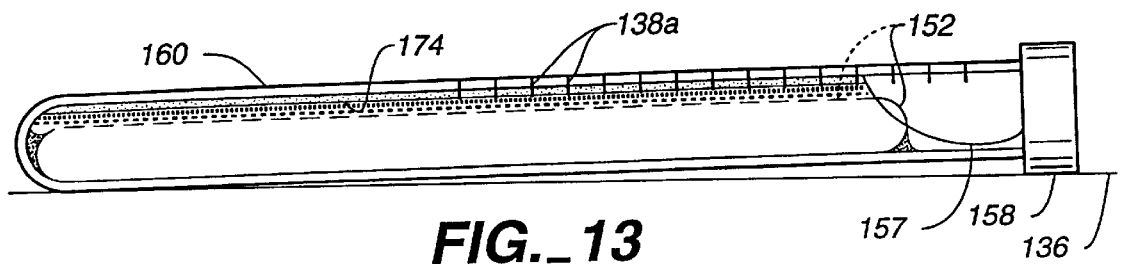
FIG._13
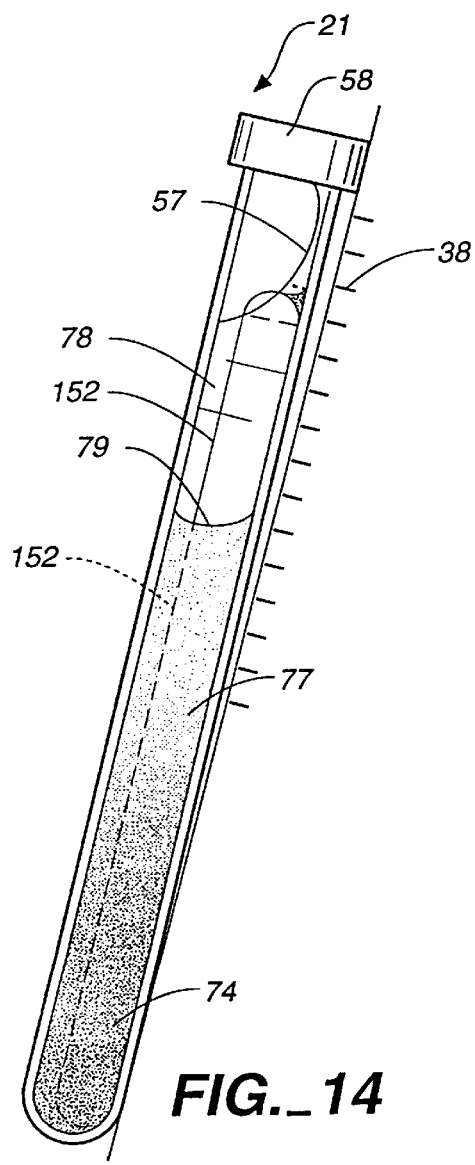
FIG._14
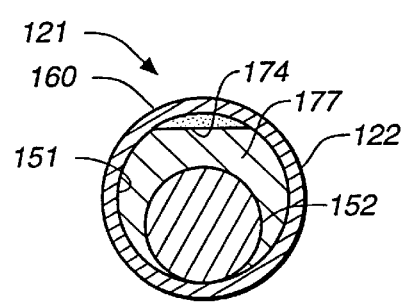
FIG._13A
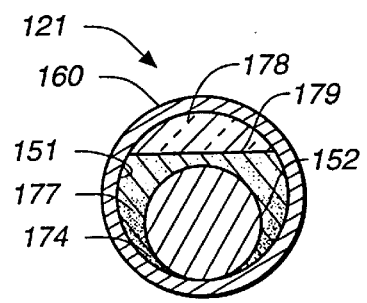
FIG._13B

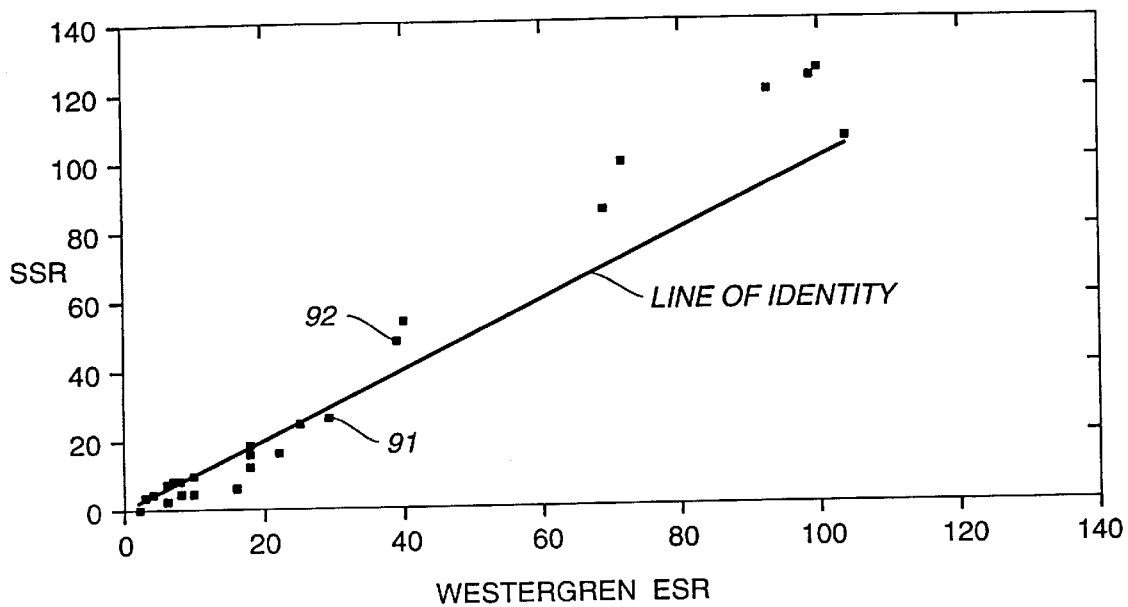
FIG._15
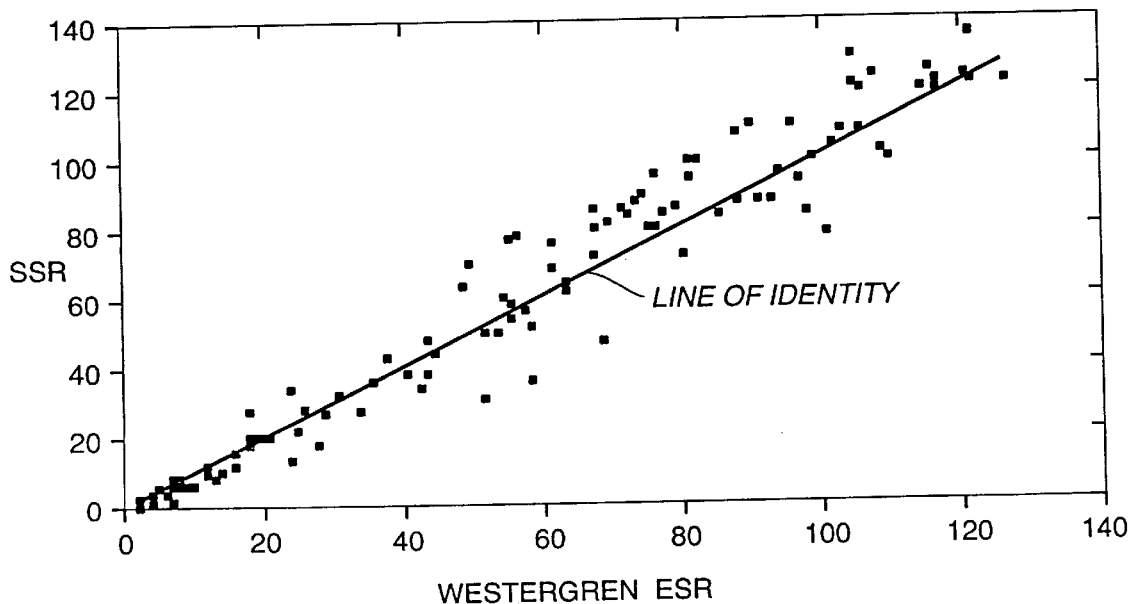
FIG._16

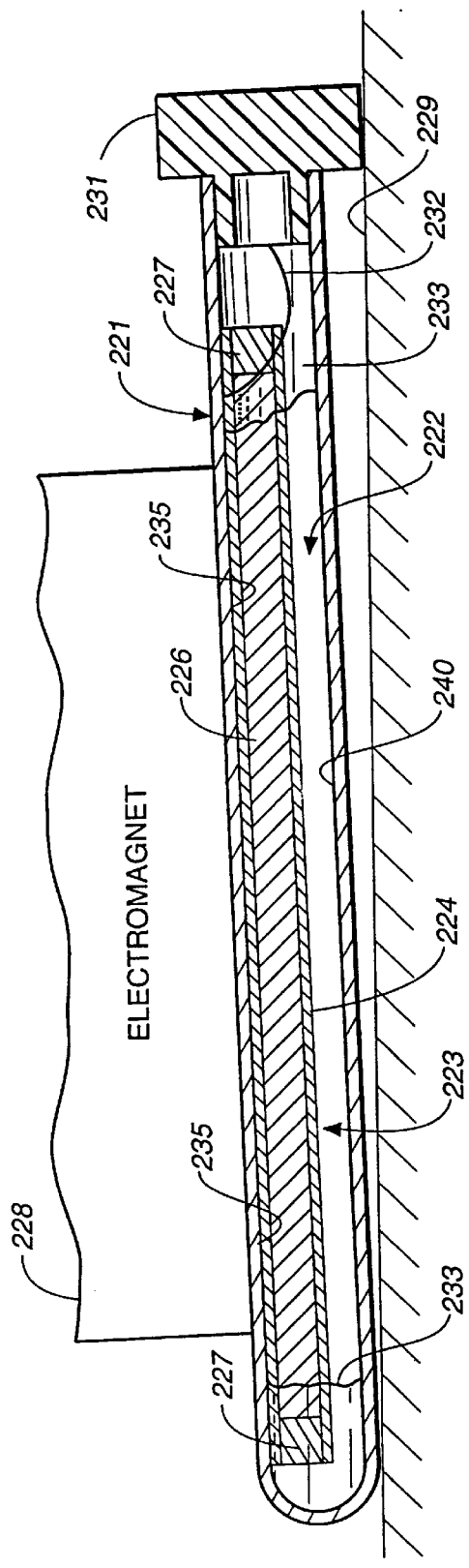
FIG._17

METHOD AND APPARATUS FOR RAPID DETERMINATION OF BLOOD SEDIMENTATION RATE

This is a continuation of Ser. No. 08/901,593 filed Jul. 28, 1997 ( now Pat. No. 5,844,128), which is a divisional of Ser. No. 08/718,632 filed Sep. 17, 1996 (now Pat. No. 5,986,461), which is a divisional of Ser. No. 08/270,681 filed Jul. 12, 1994 (now Pat. No. 5,594,164).

TECHNICAL FIELD

The present invention relates, in general, to a method and apparatus for determining the settling rate of solids in a liquid-solid mixture, and more particularly, relates to methods and apparatus for determining the erythrocyte or red blood cell sedimentation rate in whole blood.

BACKGROUND ART

The rate at which erythrocytes or red blood cells settle through blood plasma in a whole blood specimen has long been the subject of medical study. It has been found that the sedimentation rate of blood can be significantly increased by a wide range of inflammatory conditions and diseases. Various attempts have been made to automate blood sedimentation apparatus and to correlate settling or sedimentation rates and patterns to inflammatory conditions.

The original laboratory studies, however, are still regarded as the standards. More particularly, there is a Wintrobe sedimentation method and a Westergren sedimentation method. The Westergren method is most widely used and employs a 300 millimeter long settling tube with the lower 200 millimeters being graduated. The tube is filled to the 200 millimeter mark with approximately 0.8 milliliter of blood and 0.2 milliliters of anticoagulant diluent which is allowed to gravity settle over a one or a two hour period. The amount of settling in a one hour period in a Westergren settling tube is generally regarded as the standard for blood sedimentation rate.

In any blood sedimentation study the specimen is first thoroughly mixed so that the erythrocytes are evenly distributed throughout the specimen. In the Westergren method, after mixing, the 300 millimeter tube is brought to a vertical orientation for gravity settling and the settling clock started. After one hour the amount of settling which has occurred, as determined by the distance that the interface between the plasma and the erythrocytes has traveled downward, is measured.

Various attempts have been made to automate the Westergren settling process. U.S. Pat. No. 4,041,502 to Williams, et al., for example, discloses an automated sedimentation measuring system in which measurements are taken every 15 seconds for one hour (or two hours) and a blood sedimentation curve is produced as a result of these measurements. U.S. Pat. No. 4,848,900 to Kuo, et al. is a similar blood sedimentation automated system in which a blood sedimentation curve is also generated over a one hour period.

While the amount of sedimentation varies for each specimen, as influenced by inflammatory conditions, the general shape of blood sedimentation curves is quite similar as a result of the settling phenomena which are operative. Most sedimentation curves, therefore, have three phases which can be clearly identified. First, there is a "lag phase" in which settling is very slow and gradual. Next comes a "decantation phase" in which rapid, virtually linear, settling occurs. Finally, there is a "syneresis phase" in which the rate of settling greatly slows towards the end of the one hour settling period.

While the erythrocytes are more dense than the plasma, they are small and thus have such a high surface area relative to volume that they do not readily sediment through plasma as single cells. In the initial or lag phase, therefore, the erythrocytes must come in contact with each other to group together in clumps or clusters known as "rouleaux." Once a sufficient number of erythrocytes have grouped in rouleaux, the rouleaux will begin to sediment through the blood plasma toward the bottom of the sedimentation tube. Thus, the initial sedimentation or lag phase may take 5 to 15 minutes for sufficient rouleaux clusters to form to enter the more rapid decantation phase. The lag phase portion of a sedimentation vs. time curve, therefore, is relatively flat and typically shows little sedimentation or movement of the plasma-erythrocyte separation interface.

As the erythrocytes in rouleaux settle, they contact other erythrocytes which adhere and decrease the surface are to volume ratio and hence the drag on the sedimenting rouleaux. Additionally, however, the plasma at the bottom of the sedimentation tube must rise or be displaced upwardly by a volume equal to the sedimenting erythrocytes. The settling process, therefore, involves both downward migration or sedimentation of the more dense erythrocytes in rouleaux and upward migration of the lighter plasma through the downwardly migrating rouleaux. The sedimentation rate increases significantly and is fairly linear in the decantation phase or the mid-range of the sedimentation process.

Toward the end of the sedimentation process, however, the erythrocytes begin to pack more tightly at the bottom of the tube. This narrows the pathways for plasma to upwardly migrate to the plasma-erythrocyte separation boundary or interface. The plasma, therefore, has a more difficult time escaping from between the red cells in rouleaux as the packing density or hematocrit rises. Sedimentation, therefore, again slows in this last or syneresis phase of sedimentation.

Various attempts have been made to devise methods and apparatus for accelerating the determination of erythrocyte sedimentation rates. In my U.S. Pat. No. 3,824,841, for example, a sedimentation method is disclosed in which specimens are centrifuged in vertically oriented settling tubes, with the tubes periodically rotated about their longitudinal axis. The erythrocytes seesaw back and forth across the tube and downwardly under a combination of gravity and centrifugal forces. The sedimentation time using this process is reduced from one hour to about three minutes, and the sedimentation rates measured using this process and apparatus can be related to the Westergren method using non-linear regression algorithms. This apparatus and method, however, have drawbacks in the form of the complexity of the apparatus, as well as the need to use non-linear regression algorithms.

Sedimentation studies also have been undertaken in shorter tubes and particularly 100 millimeter settling tubes. The problem with this technique is that the final or syneresis phase, in which the hematocrit is rapidly rising, occurs earlier, again requiring non-linear algorithms for correlation to Westergren sedimentation results.

Additionally, accelerated blood sedimentation has been measured using tilted or inclined sedimentation tubes instead of vertically oriented tubes. Using an inclined tube (a tube 100–200 millimeters long and 2.5 millimeters in diameter inclined at about 30 or 45 degrees from vertical) settling rates can be measured after only 20 minutes of settling. The settling rate which is determined using such apparatus, however, is not a true Westergren sedimentation rate because once again the relationship between the hematocrit rise and the entrapment of plasma is altered resulting in a nonlinear relationship between the test method. Thus, the settling is non-linear and the measured rates must be related to Westergren rates by non-linear correlation algorithms. Tilting of the tube reduces the settling time by about two-thirds but because there is in this method no shortening of the lag phase, 20 minutes is still required and a non-linear correlation to Westergren rates is also necessary.

In general, the use of non-linear algorithms becomes less reliable in relating results to Westergren sedimentation rates as the sedimentation rate increases. High sedimentation rates usually indicate the presence of inflammatory conditions. Thus, the non-linear effects induced by rapid sedimentation tend to decrease the correlation accuracy to Westergren rates for specimens which are most affected by disease and other conditions sought to be discovered or analyzed by the sedimentation process.

Mixing of small volumes of liquid specimens has been found to be very difficult. One approach has been to provide a specimen container which has a septum or wall extending down most of the length of the tube except the ends. Such a structure is shown in U.S. Pat. No. 4,701,305 to Hattori et al. The Hattori et al. approach, however, requires that the specimen be urged in a loop around the septum with the result that mixing of the specimen constituents is relatively slow.

Accordingly, it is an object of the present invention to provide an apparatus and method for erythrocyte blood sedimentation which can be rapidly accomplished and yet is capable of high correlation by linear transposition to Westergren sedimentation rates.

Another object of the present invention is to provide an erythrocyte sedimentation method and apparatus which can be used repeatedly on the same specimen to rapidly determine and verify the blood sedimentation rate.

Another object of the present invention is to provide a blood sedimentation apparatus and method in which the whole blood specimen, from the moment of venipuncture, remains in a sealed container.

Still a further object of the present invention is to provide a blood sedimentation apparatus and method in which smaller blood specimens are required and mixing of the blood specimen can be readily accomplished in very small volumes.

Another object of the present invention is to provide an improved specimen container for use with processes requiring mixing of small liquid volumes.

Still another object of the blood sedimentation apparatus and method of the present invention is to provide a sedimentation process having increased accuracy, relatively low cost, and suitability for semi-automated use by relatively unskilled paramedical personnel.

The blood sedimentation method and apparatus of the present invention have other objects and features of advantage which will become apparent from, and are set forth in more detail in, the accompanying drawing and following Best Mode Of Carrying Out The Invention.

DISCLOSURE OF INVENTION

The method of the present invention provides a process for accelerated determination of erythrocyte sedimentation in whole blood which can be correlated with a very high confidence level to Westergren settling rates using linear data transposition. The present method greatly accelerates the lag phase by using one of several techniques, accomplishes the gravity decantation phase rapidly by orienting the specimen container in a manner reducing the time required for settling, and essentially eliminates the syneresis phase, again by orienting the specimen container to avoid plasma trapping as hematocrit rises.

The method for accelerated determination of erythrocyte sedimentation of the present invention comprises, briefly, inducing rouleaux formation in a time period substantially less than the Westergren lag phase time period for the same specimen and in an amount sufficient for the specimen to enter the decantation phase. In the preferred form of lag phase acceleration, a portion of the specimen is formed into a very thin cross-section in the specimen container through which a fluid current is induced to flow so that contact between individual erythrocytes is enhanced and rouleaux formation in such portion occurs rapidly. This thin cross-sectional portion of the container is advantageously provided by a rod positioned inside the lumen of a tubular container and extending beyond the top surface of the specimen to cause a veil of specimen material to form by capillary attraction between the rod and container. Moreover, the very thin cross-sectional portion of the specimen is oriented preferably at about 20 to about 30 degrees from horizontal for gravitational movement of the rapidly formed rouleaux down through the specimen to seed the specimen and commence the decantation phase.

In one alternative form of the present process, lag phase acceleration is accomplished by centrifugating the specimen, rather than creating a capillary veil, to form rouleaux rapidly. In still a further alternative process, a confined cross-sectional portion of the specimen container is used and combined with a change of the specimen container configuration to accelerate the lag phase. This form of lag phase acceleration is accomplished by holding a rod, for example magnetically, against an upper side of a horizontally oriented container lumen and then releasing the rod to gravitate down through the specimen to a lower side of the lumen.

The present process further includes the step of gravity settling the erythrocytes, after rouleaux formation, with the specimen container oriented to substantially reduce the time required for the decantation phase below that which would be required in the Westergren process for the same specimen. Such gravity settling is accomplished, for example, by maintaining the specimen container oriented at 30 degrees or less to the horizon. This orientation, together with the presence of the rod on the upper side of the tube lumen, provides two protected channels through which plasma can escape thus significantly shortening the syneresis phase of sedimentation. The method of the present invention includes as a final step determining the amount of sedimentation which has occurred in the specimen, preferably by reorienting the specimen container from its near horizontal orientation for gravity settling to a near vertical orientation for sedimentation measurement.

The apparatus for accelerated determination of erythrocyte sedimentation rate is comprised, briefly, of an elongated specimen tube having a lumen formed to contain a blood specimen therein and preferably including a very thin cross-sectional portion. The thin cross-sectional portion of the lumen advantageously can be provided by mounting a rod, adhesively or magnetically, in the specimen tube next to a wall of the tube and in a position to extend above a top surface of the specimen so that a veil of blood will form between the rod and tube wall.

The present apparatus also includes specimen tube orienting assembly which can hold the specimen tube in a manner orienting it for accelerated rouleaux formation, for example at about 30 degrees from a horizontal plane. The orienting assembly also orients the specimen tube for accelerated gravity settling during the decantation phase, again at about 30 degrees or less to a horizontal plane. Preferably the orienting assembly is further formed to enable manipulation of the specimen tube to enable specimen mixing and reorientation from a gravity settling orientation to a sedimentation determination orientation.

In a first alternative embodiment of the apparatus the orienting assembly is also formed for centrifugation of the specimen tube, and in a second alternative embodiment the orientation assembly is formed to selectively hold and release a rod mounted in the specimen tube.

In another aspect of the present invention, a specimen container for mixing small volumes of liquid, such as blood specimens, is provided. The specimen container has an elongated bore with an elongated member mounted therein to define a resulting elongated lumen with a channel portion of the cross sectional area of the lumen being formed to be sufficiently thin in transverse cross section that a liquid-mixing gas bubble cannot enter this channel portion of the lumen and the liquid can flow along the channel.

DESCRIPTION OF THE DRAWING

FIG. 1 is a top perspective view of an erythrocyte sedimentation apparatus constructed in accordance with the present invention.

FIG. 2 is a top perspective view corresponding to FIG. 1 with the blood specimen tubes oriented for accelerated rouleaux formation and gravity settling.

FIG. 3 is an enlarged, top plan view in cross section of the apparatus taken substantially along line 3—3 in FIG. 1.

FIG. 4 is a greatly enlarged, side elevation view, in cross scion, of a specimen container tube constructed in accordance with the present invention.

FIG. 5 is an end view, in cross section, taken substantially along the plane of line 5—5 in FIG. 4.

FIG. 6 is a graph of sedimentation rate data using the apparatus of FIGS. 1–5, as compared to Westergren sedimentation data for modified blood specimens from the same patients.

FIG. 7 is a top perspective view of an alternative embodiment of an erythrocyte sedimentation apparatus constructed in accordance with the present invention.

FIG. 8 is an enlarged, side elevation view, in cross section, of a specimen container designed for use with the apparatus of FIG. 7.

FIG. 9 is a further enlarged, cross sectional view taken substantially along the plane of line 9—9 in FIG. 8.

FIG. 9A is a cross sectional view corresponding to FIG. 9 of an alternative embodiment of the specimen collection tube of FIG. 8.

FIG. 9B is a cross sectional view corresponding to FIG. 9 of another alternative embodiment of the specimen collection tube of FIG. 8.

FIG. 10 is a schematic representation of the specimen tube of FIG. 8 after drawing of a specimen.

FIG. 11 is a schematic representation of the specimen tube of FIG. 8 during mixing.

FIG. 12 is a schematic representation of the specimen tube of FIG. 8 during centrifuging.

FIG. 13 is a schematic representation of the specimen tube of FIG. 2 at the start of gravity settling.

FIG. 13A is an enlarged, cross sectional view of the specimen tube at the start of settling.

FIG. 13B is an enlarged, cross sectional view of the specimen tube after significant settling has occurred.

FIG. 14 is a schematic representation of the specimen tube of FIG. 8 during the step of determining the amount of sedimentation.

FIG. 15 is a graph of sedimentation rate data using the apparatus of FIGS. 7 and 8, as compared to Westergren sedimentation data for unmodified blood specimens from the same patients.

FIG. 16 is a graph of sedimentation rate data using the apparatus of FIGS. 7 and 8, as compared to Westergren sedimentation data for modified blood specimens from the same patients.

FIG. 17 is side elevation view, in cross section of an alternative embodiment of a specimen container constructed in accordance with the present invention.

BEST MODE OF CARRYING OUT THE INVENTION

The method and apparatus of the present invention achieve rapid erythrocyte sedimentation results which can be linearly related to Westergren sedimentation results. Essentially two key principles are employed to greatly accelerate the time required for sedimentation. First, the lag phase of the conventional Westergren sedimentation method is accelerated by inducing rouleaux formation in the specimen rapidly, until there is sufficient rouleaux to cause erythrocyte settling at substantially the decantation rate for the specimen. Next, the specimen is gravity settled in a container formed and oriented so that the erythrocytes can settle through upwardly migrating plasma in a manner which is substantially unimpeded by the increasing hematocrit.

The method and apparatus of the present invention allow a blood specimen sedimentation to be accelerated across the lag phase, gravity settled through the decantation phase in a much shorter period of time, and settling in the syneresis phase to essentially be eliminated. The result is that sedimentation data that can be linearly transposed to Westergren data can be obtained in five minutes or less.

Lag Phase Acceleration

The first step of the present process is to accelerate sedimentation by greatly reducing the time which would normally be required for the specimen to pass through the lag phase and begin the linear decantation phase. Several techniques for acceleration of blood sedimentation through the lag phase have been discovered and will be described herein, but the preferred technique can be described by reference to a specimen tube which is particularly well suited for use in the method of the present and is shown in FIGS. 4 and 5. Essentially the same tube also is shown in FIGS. 8 and 9.

As will be seen from FIGS. 4 and 5, elongated specimen tube or container 21 is formed with a tube wall 22 which defines a tube lumen 23. Lumen 23 terminates in an open end 24 having a rubber stopper or other end closure member 26 mounted therein. As will be described in greater detail hereinafter, specimen tube 21 advantageously can be a partially evacuated, blood specimen tube having a length of about 110 millimeters and a lumen diameter of about 6 millimeters. An anti-coagulant is placed in the tube before the specimen is drawn. The specimen is taken by a needle 159 (shown in broken lines in FIG. 8) which extends through stopper 26 in a conventional manner, and such blood specimen tubes, as thus far described and blood specimen drawing techniques, are well known in the medical profession.

While the present process is described by reference to preferred specimen tube 21, it will be apparent from the following description that other forms of blood specimen containers can be used in the present process.

In order to provide several important advantages, as will be set forth below and, particularly in order to provide a very thin cross-sectional portion of the specimen in lumen 23, tube 21 preferably has an elongated member or rod 27 mounted in the lumen. Rod 27 is preferably about 4 millimeters in diameter and is secured or held by adhesive, fused glass or other means, against one side of lumen 23, in this case the upwardly oriented side 28.

In the preferred form, tube 21 has a substantially cylindrical lumen 23 and elongated member 27 is a cylindrical rod, but other lumen-rod configurations are suitable for use in the present invention.

As set forth in the background, the Westergren lag phase can require 5 to 15 minutes to complete. During this time rouleaux must be formed from individual erythrocytes in sufficient number to seed the specimen and start the linear or decantation phase of sedimentation.

In the present invention rouleaux formation is induced at an accelerated rate and sufficient rouleaux created to begin the decantation phase in a matter of seconds, for example, 30 seconds or less. The preferred manner of accelerating rouleaux formation is to provide a specimen container which will have a very thin cross-sectional area in one portion of lumen 23. As will be seen in FIG. 5, the combination of cylindrical rod 27 and cylindrical lumen 23 is that two areas of small cross-section, namely, horn-like areas 31 and 32, exist proximate upper side 28 of lumen 23. Thus, blood specimen 29 in these areas is at least somewhat confined. While it may appear that horn-shaped cross-sectional areas 31 and 32 are "small" or "thin" in cross section, in the absence of lengthwise current induced by the exaggerated settling of rouleaux in the veils, they do not by themselves produce the accelerated rouleaux formation of the method of the present invention.

As shown in FIG. 4, upper end 33 of rod 27 protrudes above top surface 34 or the meniscus of specimen 29 for a tube oriented as shown, in this case, oriented at an angle of 30 degrees to a horizontal plane 36. As will be seen, the blood specimen forms an arcuate veil-like volume 37 in each of horn areas 31 and 32 proximate and up to the upper end 33 of rod 27. While impractical to show in the drawing, very thin specimen veil 37 will extend up rod 27 by capillary action to the last point of contact 38 of the rod with tube upper side wall 22.

As arcuate specimen veil 37 extends upwardly toward point 38, its cross section thins and in fact tapers down to what is believed to be a relatively small multiple of the red cell diameter, for example, a veil cross section of 10 cell diameters (70–80 microns) or less. Thus, in the area of specimen veil 37 red cells are forced to be in such close proximity to each other that they cluster and form rouleaux in a few seconds. For example, substantially all the red cells in the thinnest upper regions of veil 37 are believed to be in rouleaux in 15 seconds.

Obviously, however, the amount of the specimen in the upper reaches of veil region 37 is small as compared to the entire specimen 29. It is believed, however, that rouleaux are starting to form elsewhere in the specimen and particularly in small cross-sectional horns 31 and 32 all along the rod. This rouleaux formation is probably somewhat accelerated as compared to formation in a Westergren tube, but it still would result in an undesirably slow lag phase. Nevertheless, specimen 29 enters the decantation or linear sedimentation phase almost immediately after rouleaux formation has been completed in the upper end of veil region 37 when specimen tube 21 is held in the 30 degree orientation shown in FIG. 4.

It is hypothesized that the rouleaux formed in very thin upper region of veil 37 are immediately free to gravitate downwardly along veil 37 and across rod 27, and as they do so plasma is pulled up along horned regions 31 and 32 between the rod and tube and into veil region 37. The orientation of tube 21 is such that rouleaux can escape veil region 37 and plasma can enter the veil region. There rapidly begins to occur, therefore, a circulation pattern in which denser rouleaux settle down through and "seed" the specimen picking up more cells as they fall and yet not trapping plasma below. The plasma, on the other hand rises up the tube along horns and replaces the downwardly settling rouleaux. As the plasma rises, its motion is believed to cause free erythrocytes to agglomerate with partially formed rouleaux all along horns 31 and 32, thus causing further rouleaux formation and sedimentation.

The exact mechanics of acceleration are not known, but in a blood specimen of high sedimentation rate within about 30 seconds flow of plasma upwardly along horns 31 and 32 toward veil 37 can be clearly seen in specimen 29 and rouleaux clearly has formed in an amount sufficient to cause the entire specimen to be in the decantation phase.

At the present time many aspects of this technique for accelerating rouleaux formation are unknown. It is known, however, that the same specimen tube assembly will require 15 minutes to complete the decantation phase when rod 27 does not extend above specimen top surface 34 and only 5 minutes when it does extend above surface 34. Thus, if the horn regions 31 and 32 are used alone the specimen can be settled in ¼ the time of a Westergren sedimentation test, but if the specimen cross section is further thinned by extending rod 27 beyond surface 34 to form veil region 37, the sedimentation time can be reduced to 1/12 of the Westergren sedimentation time.

It is believed that rod 27 should extend above upper specimen meniscus by at least 3 to 4 millimeters for optimum acceleration effect, but any protrusion starts to provide a thinned capillary veil which should be useful. The maximum useful protrusion similarly is not known, but blood specimens will rise up to an inch or more above meniscus surface 34 along thin capillary-like channels, such as horns 31 and 32.

As will be appreciated, various other specimen tube configurations are possible to produce a very thin capillary cross section. Converging planar walls and converging planar and curvalinear walls may provide the same effect, and such structures can be provided by lumen inserts or integrally formed tube wall configurations. To achieve the best results, it is believed to be advantageous to employ capillary forces to form, with a portion of the tube lumen, a thin veil or film of the specimen. Such a veil or film, however, also must be positioned, it is believed, so that the rapidly formed rouleaux are free to escape film or veil region 37 and seed the specimen, preferably while plasma is free to enter the film or veil portion of the lumen.

At the present time the orientation of tube 21 which is best suited for both accelerated rouleaux formation and gravity settling during the decantation phase is believed to be between about 20 degrees to about 35 degrees from the horizon. Most preferably tube 21 is oriented at about 30 degrees from horizontal plane 36 during both accelerated rouleaux formation and gravity settling during the decantation phase. As tube 21 is lowered to an orientation below about 25 degrees, circulation of plasma up along horns 31 and 32 is reduced and sedimentation times begin to increase. Similarly, as tube orientation is increased to above about 35 degrees egress of plasma becomes impeded by settling of red cell aggregates which, at these higher angles no longer seed the sedimentation process but instead impede plasma egress.

Rapid Decantation and Syneresis Elimination

The next step in the process of the present invention is to gravity settle the specimen, which is now through the lag phase of sedimentation. The middle or decantation phase tends to be relatively linear until the hematocrit increases significantly and the settled erythrocytes trap or impede upward migration of plasma at the bottom of the specimen tube, that is the specimen enters the syneresis phase.

In the present process, specimen container 21 is oriented in a manner enabling settling of erythrocyte cells through upwardly migrating plasma without trapping or impeding of the plasma as a result of the relatively small transverse cross sectional area of the tube. Westergren tubes, and settling tube 21, both have relatively small diameters in order that the amount of whole blood required to perform sedimentation testing can be minimized, but it is the small diameter which causes the slowing of sedimentation at the end of the settling period. In the present invention the time required for the linear decantation phase is greatly shortened and the syneresis phase is substantially eliminated by orienting specimen tube 21 with its longitudinal axis 55 of specimen tube 21 in a near horizontal orientation, as shown in FIG. 4. As used herein, "near horizontal" shall mean between about 35 degrees and about zero degrees from the horizon. Orienting longitudinal axis 55 in a near horizontal plane cause the transverse area of specimen tube 21 to be greatly increased as compared to the transverse area (FIG. 5) of a vertically-oriented tube 21.

Such an orientation of the specimen tube 21 will cause the rouleaux in the specimen tube to simultaneously gravitate or fall across the relatively small diameter of the tube, but over a relatively large area of the tube. The resistance to downward movement of rouleaux and to upward migration of plasma in the tube as a result of the large horizontal area of the near-horizontal, elongated tube substantially eliminates impeding, choking or slowing down of the sedimentation rate. The syneresis phase, as a result of dramatically increasing hematocrit and resultant trapping of plasma by the erythrocytes, is substantially eliminated. By orienting the settling tube in a near horizontal orientation, the rouleaux move or settle down through the plasma in a manner which is very close to or approximates settling in a bottomless tube. The hematocrit or blood cell packing density buildup has very little effect in trapping plasma because of the large transverse or horizontal area and of the very short distance need for plasma travel to escape the settling erythrocytes.

Moreover, since the distance across the tube diameter is short, the time required for completion of the decantation or linear settling phase is much less. It has been determined that, after about 3.5 to about 5.0 minutes of gravity settling with the specimen tube in a horizontal orientation, the decantation or linear sedimentation phase is completed in a degree which is substantially equal to, and correlatable with, 60 minutes of settling using the Westergren method.

Sedimentation Determination

The next step in the process of the present invention, therefore, is to determine the amount of settling which has occurred during the period of time which the lag phase was accelerated and the decantation phase was taking place, for example, 5.0 minutes. In order to facilitate a determination of the amount of settling which has occurred, it is preferable to reorient specimen container 21 to a near vertical position. Thus, tube 21 can be rotated to a near vertical orientation, for example, to about 90 degrees from the horizon. This causes the settled erythrocytes to slip down the bottom side of the specimen tube 21 and the plasma on upper side of lumen 23 to float up the opposite side of the tube to the top.

The reorientation of the specimen tube to a near vertical position will cause the settled cells to reach the bottom of the tube quickly, and a measurement of the separation boundary or interface between the plasma and settled cells can be takes, for example, as soon as five seconds after reaching a vertical orientation. In the vertical orientation the location of the separation boundary between plasma and erythrocytes can be more accurately determined than in the near horizontal orientation. The tube may, however, be read in a semi-vertical position with a modest increase in associated reading error. As described above, the steps of accelerated induction of rouleaux formation, gravity settling in an orientation shortening the decantation phase and determining the amount of settling can be implemented by hand by a laboratory technician. By simply employing a rack or tube support structure which will hold tubes 21 in the orientation of FIG. 4 and then a second rack which can be used to vertically orient the tubes, a technician can easily perform the procedure of the present invention without automation or special equipment.

Semi-Automated Sedimentation Apparatus

Nevertheless, it is an important feature of the present invention that the method of the present invention can be easily semi-automated. FIGS. 1 through 3 show one form of sedimentation tube manipulating apparatus 20 which can be used to perform the present process. Sedimentation apparatus 20 preferably includes a base 41 having leveling assembly, such as manually engageable leveling screws 42 and a spirit level 43, so that the apparatus can be leveled for reproducible results on a laboratory bench top. Mounted on base 41 is a housing 43 which preferably includes a translucent front panel 44 behind which a light source, such as two U-shaped fluorescent tubes 46 and 47 (FIG. 3), are positioned.

In order to enable proper orientation and manipulation of sedimentation tubes 21 and 22, a rotatable tube holder assembly, generally designated 48, is mounted to extend from front panel 44 of housing 43. In the form of sedimentation apparatus 20 illustrated, assembly 48 includes a central U-shaped frame member 49 mounted by collar 51 to a shaft 52 for rotation therewith. Secured by fasteners to U-shaped frame member 49 are tube holder members 53 and 54. Each of the tube holder housings 53 and 54 includes a slotted or windowed front opening 56 with sedimentation measuring indicia 57 positioned closely proximate thereto. As best may be seen in FIG. 3, the back side 58 of housings 53 and 54 is open so that light may enter the housing and fall upon tubes 21. Housings 53 and 54 further include two mounting support felts (not shown) which receive and firmly hold the tubes in the housings without interfering with the passage of light through the tubes and out slots 56. As will be seen from FIG. 3, the tubes 21 are mounted in housings 53 and 54 with rod 27 on the same side of the respective housings so that when assembly 48 is stopped in the position shown in FIG. 2, rods 27 will be oriented inside tubes 21 essentially as shown in FIG. 4.

Shaft 52 extends through front wall 44 of housing 43 and completely through the housing and out back wall 59. A first spur gear 61 is mounted on the end of shaft 52 and cooperatively engages a pinion 63 carried by shaft 64 of motor 66. Mounted interiorly of housing 43 is an indexing disk 67 which is fixed for rotation with shaft 52 by collar 68. Also mounted interiorly of housing 43 is a magnet 69 and a ferromagnetic collar 71 coupled to shaft 52. Finally, an indexing detent assembly 72 and light ballasts 73 also are mounted inside housing 43.

Operation of sedimentation apparatus 20 to implement the method of the present invention can now be described. In the preferred form, the first step of the present invention is to thoroughly mix specimen 29 in specimen tube 21. Mixing insures that there is no pre-formed rouleaux in the specimen, and mixing thoroughly mixes the anti-coagulant material in the specimen tube with the whole blood that has been drawn. Apparatus 20, therefore, preferably is constructed in a manner which will manipulate tube 21 so as to effect mixing.

As will be set forth in more detail below, one of the substantial advantages of the construction of specimen tube 21 in which rod 27 is positioned in lumen 23 is that the gas bubble which will always be present in the tube can be used as a mixing device. Thus, by inverting tube 21 the bubble will move from one end of the tube to the other, with the blood/anti-coagulant moving in the opposite direction. One of the substantial problems in connection with mixing small liquid volumes is that in small diameter tubes gas bubbles or the like will bridge, rather than move up and down the tube, and prevent mixing. The presence of the rod in lumen 23 enables the blood/anti-coagulant to pass beyond the bubble in horn regions 31 and 32, because the bubble cannot enter into the thin transverse cross section horn regions.

As a first step, therefore, motor switch 74 can be turned on and the motor 66 will slowly rotate the holder assembly 48 when the shaft and gears are in the solid line positions shown in FIG. 3. Thus, gear 61 is engaged with gear 63 and assembly 48 is positioned out away from front panel 44 of housing 43. The gearing and motor speed can be set so that rotation occurs at about 3 rpm or 6 inversions per minute. About three minutes of rotation will insure that the specimens in tube holder assembly 48 are thoroughly mixed.

In a semi-automated process the technician merely turns switch 74 off after about three minutes of mixing. In a more fully automated process, termination of the mixing cycle is controlled by a timer. The gears 61 and 63 can be retained in interengagement by magnetic member 69 which attracts collar 71 thereto and maintains shaft 52 and gear 61 in the solid line position of FIG. 3.

Once mixing is complete, the technician can push the shaft inwardly to the dotted line position shown in FIG. 3, freeing collar 71 from magnetic attraction of magnet 69 and freeing gear 61 from pinion 63. As tube holder assembly 48 is pushed inwardly towards panel 44, indexing disk 67 also is moved to the dotted line position at which it is engaged by indexing detent assembly 72. Detent disk 67 can have two notches which receive detent element 76 when the notches are in indexed relation to element 76. The indexing disk 67 is fixed by a collar for rotation with shaft 52 and has a first notch at a location which will secure tube holder assembly 48 in the position shown in FIG. 2, namely, at an angle of about 30 degrees to a horizontal plane. A second notch is provided in indexing disk 67 which will hold tube holder assembly 48 in the position of FIG. 1, namely, in a near vertical position.

Accordingly, in a semi-automated system, the technician turns motor switch 74 off, pushes tube holder assembly 48 inwardly to a position closely adjacent to translucent front panel 44 and rotates the assembly to the position of FIG. 2, at which it is held in place by detent element 76 engaging a notch indexing disk 67. The assembly is left in this position for five minutes. The technician can then manually rotate assembly 48 from the FIG. 2 position to the FIG. 1 position, at which point detent 76 will engage a second notch indexing disk 67, holding the assembly as shown in FIG. 1. The technician can then read the location of the plasma/erythrocyte interface using indicia 57 on the front of tube holder housings 53 and 54.

One of the important and highly advantageous aspects of the present invention is that each blood specimen 29 can repeatedly have its sedimentation rate tested. Accordingly, the technician normally will complete the measurement process and then return the tube holder assembly to the FIG. 3 solid line position and turn on the motor to re-mix the specimen. It should be noted, of course, that light switch 77 should be turned on so that reading of the plasma/erythrocyte interface or boundary can be easily accomplished by back lighting of the specimen through opening 58.

Using the apparatus of FIG. 1, therefore, a technician could easily obtain six or seven sedimentation readings in the time period required to obtain one reading using the Westergren process, including the time required to re-mix the specimen after each sedimentation determination.

As will be appreciated, displacement of assembly 48 between the solid and dotted line position shown at FIG. 3 also can be fully automated, and it would also be possible to automate the determination of the location of the plasma/erythrocyte interface. Thus, automated optical reading assemblies can be positioned proximate tubes 21 in more sophisticated systems so that the entire process, including registration/recording of sedimentation results can be automated.

FIG. 6 shows a graph of sedimentation results obtained using apparatus 20 and the process of the present invention. These results have been compared to Westergren sedimentation rates for the same specimens. The specimens are whole blood specimens which have been modified in the laboratory to change their sedimentation rate in a manner well known and set forth in the blood sedimentation literature. As will be seen, using apparatus 20 and the method of the present invention one can simply multiply the results of use of the present apparatus by 2.0 over the full range of sedimentation and obtain Westergren sedimentation rates. The best fit line for data taken using the present apparatus and method is not significantly different from a line of identity with the Westergren rates, that is, the $r^2$ variation is equal to 0.98.

Specimen Container

One of the problems which is particularly acute with blood specimen sedimentation studies is that it is highly desirable to minimize the amount of the specimen which is drawn. If a small volume of blood specimen is placed in an elongated specimen container, however, it is relatively difficult to effect mixing of the specimen, even when diluted with anticoagulant. Long thin specimen containers with low volumes of blood will not readily allow a bubble to migrate from one end of the container to the other. Even beads or balls are sometimes difficult to employ as gravity mixing devices in small diameter elongated tubes and such mixing devices may damage red cells and cause a release of hemoglobin.

In an additional broad aspect of the present invention, therefore, a method and apparatus for mixing constituents of a small volume of liquid in a container having a small cross section is provided by the preferred form of specimen tube 21 and 121 of the present invention, as shown in FIGS. 4 and 8 of the drawings. Specimen tubes 21, 121 can be elongated tubular members having a central lumen 23, 151 extending along the length of the tube. An elongated member 27, 152 is mounted in the lumen and preferably extends over a majority of the length of the lumen. Elongated member 27, 152 can be secured to an interior surface of the tube along one side of the tube, for example, by an ultraviolet-activated adhesive 153, or by other means, such as fusing a glass member to the interior of a glass tube, or magnetically holding the rod to a side of the tube, which will be described in more detail hereinafter.

The mixing advantages of tube 21, 121 will be described by reference to FIGS. 8 and 9 and tube 121, but it will be understood that tube 21 is similarly constructed. As best may be seen in FIG. 9, the specimen tube wall 150 and member 152 define therebetween a lumen 151 having a transverse cross section configuration which will prevent a gas bubble from completely filling the cross section of the lumen, which would prevent the liquid from passing beyond the gas bubble as it rises in the tube. This can be accomplished, for example, by providing a wedge-shaped transverse area. As will be seen in FIG. 8, the use of a tube 121 having a cylindrical bore with an elongated cylindrical rod 152 mounted therein will define therebetween a lumen 151 which is crescent-shaped in transverse cross section and has two wedge-shaped horn regions or converging areas 156 at ends of the crescent.

Lumen 151, therefore, has two side-by-side longitudinally extending lumen portions which are in open, septum-free, fluid communication with each other over their lengths. When a mixing bubble 157 is present in a specimen tube constructed as shown for tube 121, surface tension forces will prevent the air bubble from extending into the converging wedge-shaped crescent ends 156 one of the longitudinally extending lumen portions of the cross sectional area. As specimen tube 121 is tilted, therefore, bubble 157 will migrate up the length of the tube in the widest or reminder lumen portion of the cross section of crescent 154 while the liquid, blood and anticoagulant, will migrate down the tube past the bubble in the horn regions or wedge-shaped ends 156 into which the bubble cannot extend. Thus, even in volumes as low as 1.2 milliliters in specimen containers having a diameter of only 6 millimeters, tilting of the specimen tube back and forth by sedimentation apparatus 120, or rotation by apparatus 20, will allow bubble 157 to be very effective in mixing the liquid constituents in the container.

In the preferred form, therefore, specimen tube 121 are vacuum tubes which contains a predetermined amount of specimen diluent, such as, about 0.25 milliliters anticoagulant material, suitable for mixing with a 1.0 milliliter volume of whole blood. Such vacuum tubes with anticoagulant and a vacuum which will draw a predetermined known amount of blood specimen are well known in the art. These vacuum tubes do not have elongated member 27, 152 mounted therein. The vacuum tube container 21, 121 of the present invention, therefore, includes a rubber end stopper 26, 158 through which a needle 159 can be inserted. The inner end 161 of the needle preferably should not contact the outermost end 162 of member 152. Thus, end 162 of member 152 is recessed by an amount (for example, one-half centimeter) to allow inner end 161 of needle 159 to clear member 152.

Since it is not possible to draw a perfect vacuum inside specimen tube 121, there will always be some gas, usually air, trapped in the vacuum tube. When a specimen is drawn, therefore, it will be pulled into lumen 151 by the vacuum therein until the lumen between the tube and elongated member is substantially filled (about 1.25 milliliters), with the exception of a small air bubble 157. Air bubble 157 can then be used to mix liquid after needle 159 is removed from rubber stopper 158.

A major advantage of specimen container 21, 121 and the method and apparatus of the present invention is that at all times the blood specimen is sealed in container 21, 121. Thus, the danger to technicians from handling whole blood is greatly reduced. Moreover, the same specimen can be used in the sealed container to repeat the sedimentation process.

As will be seen from FIG. 8, specimen tube 121 includes a stopper 58 having a diameter greater than the tube body. This will result in a slight tilt to the specimen tube, for example, of 2–4 degrees, from the horizon when tube 121 is placed in a horizontally oriented trough 137. This has the advantage that it ensures that bubble 157 will be up at stopper 158 so that the bubble will not cause remixing when the tube is reoriented to a near vertical orientation to determine the amount of settling. It is a feature of the present process, therefore, to effect gravity settling with container 121 oriented with upper end or stopper 158 tilted up from horizontal by about 1 degree to about 6 degrees.

Referring now to FIG. 9A, still a further alternative embodiment 121a of the specimen container of the present invention is shown. An elongated plastic insert member 181 is positioned in lumen 151a of tube 121a. The plastic insert includes horn regions or wedge-shaped cross sectional areas 156a into which a gas cannot extend. Thus, the liquid in tube 121a will pass beyond the gas bubble in areas 156a as the tube is tilted. It is believed that a tube constructed as shown in FIG. 9A, if oriented with one horn region 156a uppermost, and if a very thin section extended upwardly beyond the specimen upper surface 34, would accelerate rouleaux formation and be suitable for use in apparatus 21.

Still a further alternative tube embodiment is shown in FIG. 9B. Tube 121b has been formed to provide the narrow cross sectional areas 156b by, for example, deforming a heated glass tube to provide narrow areas 156b. Again, areas 156b are sufficiently narrow to prevent a gas from entering these areas, and the liquid can move past the bubble in these areas. Whether or not glass fabrication techniques will allow a sufficiently thin horn region 156 to be formed to allow use of the accelerated rouleaux formation technique described in connection with FIGS. 4 and 5 is unknown.

First Alternative Lag Phase Acceleration Process and Apparatus

While the preferred form of the method and apparatus of the present invention have been described in connection with FIGS. 1–6, it also has been discovered that there are alternative ways for accelerating the lag phase of blood sedimentation, and the principles of shortening the decantation phase by orienting the specimen tube in a near horizontal position can be combined with these various alternative lag phase shortening techniques. Such alternative techniques are believed to have disadvantages in connection with the apparatus which implement them, but they do produce accurate data in a short time which can be linearly correlated to Westergren sedimentation rates. Accordingly, for some applications, these alternate embodiments may have certain advantages.

Referring now to FIG. 7, an alternate sedimentation apparatus constructed in accordance with the present invention is shown. Sedimentation apparatus 120 preferably employs a centrifuge assembly as a means for inducing rouleaux formation in the blood specimen. Thus, centrifuge assembly 122 includes a rotatable turntable 124 on which tube receiving head 126 is mounted. A plurality of elongated tube receiving notches 127 are formed in head 126 and a tube retaining means, such as brand 128, can be mounted over head 126 so as to retain specimen tubes 121 in notches 126 during rotation of the centrifuge. Various other forms of tube retaining structures are suitable for use with centrifuge 122. Turntable 124 is mounted to a drive controller assembly 129. Power can be controlled through on-off switch 131, the spin rate by control knob 130 and the spin duration through knob 135.

Centrifuge assembly 122 of the present invention can be provided by any one of a number of standard laboratory centrifuges as long as they are capable of spinning elongated specimen tubes 121 with the longitudinal axis thereof generally parallel to the spin axis of the centrifuge at a rate high enough to induce rouleaux formation in an amount sufficient to cause erythrocyte settling to begin at substantially the decantation rate for the specimen in a short period of time.

Centrifuge assembly 122 accelerates the specimen with a centrifugal force that preferably is in the range of about 5 to 10 times the acceleration of gravity, g. A centrifuge operating at about 400 rpm with a distance from the spin axis to the center of the specimen tube of about 4 centimeters will produce sufficient centrifugal force to cause the somewhat more dense erythrocytes to migrate through the plasma to the outermost surface defining the specimen tube bore or lumen. As the erythrocytes are driven to the tube side, they come in contact with each other and begin to adhere together to form rouleaux which are held against the outer side of the lumen by the centrifugal force. After about 20 to 45 seconds, sufficient rouleaux will be formed on the outer side of the specimen tube lumen so that, if the rouleaux are allowed to gravitate, they will begin settling of the specimen at the decantation rate.

As above described, the next step in the process of the present invention is to gravity settle the specimen, which is now through the lag phase of sedimentation. Specimen container 121 again is oriented in a manner for settling of erythrocyte cells through upwardly migrating plasma without being constricted or impeded by the relatively small cross sectional area of tube 121. This can be accomplished using the preferred elongated, small diameter specimen tube by placing the specimen tube in manipulation apparatus 123 with the longitudinal axis 155 of specimen tube 121 in a near horizontal orientation, in this case essentially zero degrees or in a horizontal plane, as shown in FIGS. 7 and 8. Orienting axis 155 in a substantially horizontal plane cause the transverse area of the specimen tube to be greatly increased as compared to a vertically-oriented tube 121. Additionally, the outer side 160 of the specimen tube, against which the rouleaux were formed by centrifugation, is oriented in an uppermost position. Thus, specimen tubes 121 are transferred from centrifuge head 126 to a support member 136, which has a plurality of tube-receiving mounting structures, such as troughs or grooves 137. Specimen container 121 is oriented with its longitudinal axis 155 horizontal and side 160, which was facing outwardly in the centrifuge, facing upwardly on tube support member 136. This results in rod 152 in tube 121 being on bottom side 150 of the tube, which is just opposite of the position of rod 27 in tube 21 during decantation.

Again, the distance across the tube diameter is short, and the time required for completion of the decantation or linear settling phase is much less than for the Westergren process. After about 3.5 minutes of gravity settling the specimen tube 12 in a horizontal orientation, the decantation or linear sedimentation phase is completed to a degree which is substantially equal to, and correlatable with, 60 minutes of settling using the Westergren method.

In order to facilitate a determination of the amount of settling which has occurred, it is preferable that sedimentation apparatus 120 reorient specimen container 121 to a near vertical position. Thus, over a time interval of approximately 15 to 40 seconds, support member 136 can be rotated to a near vertical orientation, for example, to about 80 degrees from the horizon. This causes the settled erythrocytes to slip down the bottom side of the specimen tube 121 and the plasma on upper side 160 of the lumen 151 to float up the opposite side of the tube to the top.

It has been found that reorientation of the specimen tube 121 to a near vertical position must be accomplished more slowly than reorientation of tube 21 in order to avoid re-mixing of settled cells. Once in the vertical orientation, however, the location of the separation boundary between plasma and erythrocytes can be accurately determined using scale 138 next to troughs 137.

As will be apparent from FIG. 7, container orientation assembly 123 preferably includes support axle 139 and control and motor assembly 141 which can be used to rotate tube support member 136 from a horizontal to a near vertical position in a slow but smooth reorienting step. Apparatus 123 also may include means (not shown) for retaining each of tubes 121 in troughs 137 during their orientation to a near vertical position, although since they do not go beyond vertical, tubes 121 can be retained in troughs 137 by means of gravity.

In the method of the present invention, it is preferable that the step of mixing the blood specimen be undertaken immediately prior to inducing rouleaux formation. Thus, sedimentation apparatus 120, and particularly container-orienting apparatus 123, of the present invention preferably is formed to mix the blood specimen thoroughly just prior to the centrifuging or rouleaux inducing step.

Sedimentation apparatus 120 preferably includes a controller 141, which includes a mixer input 142 that will cause tube support member 136 to oscillate about a horizontal axis, for example, about axle 139. Such oscillation or tilting can be used to cause a gas bubble or a glass bead (not shown) to migrate from one end of specimen container 121 to the other. It would also be possible to effect mixing by a continuing rotating process, but then retention means for the specimen containers clearly would be required. In the preferred form, an air bubble in the specimen container is allowed to migrate from one end of the container to the other by tilting specimen container 121 by about 60 degrees to 75 degrees from the horizon in one direction and then by about the same amount from the horizon in the opposite direction. Such tilting can take place at about six inversions or full swings per minute for approximately two minutes. The number of tilt cycles can be adjusted by knob 145.

Referring now to FIGS. 10 through 14, details of the process of the present invention and operation of the sedimentation apparatus 120 can be more fully described.

FIG. 10 schematically illustrates specimen tube 121 immediately after obtaining a specimen of whole blood and removal of needle 159. Container 121, a 110 millimeter long tube with a 6 millimeter internal diameter bore and a 4 millimeter diameter rod in it, is filled with whole blood and diluent 171, as well as an air bubble 157, which represents the air left in the incompletely evacuated specimen tube. Specimen tube 121 is placed in tube orienting apparatus 123 in one of the grooves or troughs 137 in tray 136. The technician then can turn on the orientation device 123 by switching switch 140 to start the mixing process. Mixer light 142 will come "on" and the specimen tube is tilted about axle 139 above and below the horizon by about 70 degrees, as schematically illustrated in FIG. 11. Bubble 157 migrates through specimen 171 along the member 152 as the liquid specimen passes beyond the bubble in the crescents created by the rod 152 positioned in bore 151 of tube 121. The mixing process is continued at six inversions per minute for approximately 2 minutes, at which time controller 141 for the mixer brings tube supporting tray 136 to a horizontal stationary position and turns off mixing light 142. It may be necessary for controller 141 to slow the rate of tilting or even stop at the extremes of the cycle to allow effective mixing, particularly of contents proximate the tube ends.

The technician then lifts tube 121 from tray 136 and places the same in one of the notches 127 of centrifuge head 126. The operator turns the centrifuge "on," using actuator button 131, and the tube will be spun about a spin axis 172, as schematically illustrated in FIG. 12. The spin rate will typically be 400 rpm at a radius 173 of 4 centimeters. Centrifugation continues for approximately 20 seconds, which will cause a layer of rouleaux, schematically illustrated at 174, to form along the outermost side 160 of tube bore 151. Bubble 157 will be present at the top of the tube, and the tube will be oriented in centrifuge head 126 with the rod 152 closest to spin axis 172 so that the rouleaux will be induced to form and collect against the tube wall farthest from rod member 152.

Once the centrifuge step is completed, the technician will remove specimen tube 121 from centrifuge 126 and place the same in troughs 137 of tube orienting assembly 123, namely, in a near horizontal orientation as shown in FIG. 13. Preferably, there is no more than about 6 degrees upward tilt of the stopper end induced by a combination of stopper 158 and the trough orientation. Some upward tilt is advantageous in that it ensures that air bubble 157 will be located just under the stopper. It will be seen from FIG. 13 that rouleaux layer 174 and side 160 which was outermost in the centrifuge will be oriented in the uppermost position. Conversely, rod 152 is now in a lowermost position. Air bubble 157 will be located at the top of the tube under stopper 158. The technician can then press actuator button 171, and the tray orienting controller 141 will hold the tray in a generally horizontal position for approximately 3.5 minutes.

FIG. 13A shows the specimen in tube 121 at the start of gravity settling. Rouleaux 174 can be seen to be collected proximate the uppermost side 160 of the tube and the remainder of the specimen 177 is comprised of a mixture of erythrocytes and plasma in suspension. The centrifugation step, however, has created sufficient rouleaux that upon placement of the tube in the horizontal position on tray 136 rouleaux will begin to settle or gravitate downwardly through mixture 177 of plasma and red blood cells. In a manner analogous to cloud seeding, as the rouleaux begins to fall through mixture 177, additional erythrocytes adhere to the falling clusters and additional rouleaux are formed. The specimen undergoes the relatively linear decantation phase in which settling or sedimentation occurs relatively rapidly.

At the end of a predetermined gravity settling period, for example, 3.5 minutes, the specimen will have the appearance as schematically illustrated in FIG. 13B. The bottom of the crescents of lumen 154 will be filled with sedimented erythrocytes, largely in rouleaux 174. A middle area of the specimen will contain a mixture 177 of plasma and erythrocytes in which rouleaux are less densely packed. Finally, a layer of plasma 178 will be present proximate uppermost side 160 of specimen tube 121. A separation boundary 179 also will be present between plasma 178 and the remainder of the specimen including erythrocytes.

The final step in the method of the present invention, therefore, is to measure the amount of settling which has occurred during the gravity settling period. This can be theoretically accomplished by measuring the location of separation boundary 179 while the specimen tube is still horizontally oriented. As a practical matter, however, determination of the precise quantity of settling is less accurate when specimen tube is horizontally oriented. Thus, it is preferable that the step of determining the amount of settling be accomplished by reorienting the specimen tube to the position shown in FIG. 14, namely a near vertical orientation. Such reorientation is accomplished automatically after 3.5 minutes of gravity settling by controller 141, which smoothly and gradually tilts tray member 136 to a near vertical position, for example, to 80 degrees above the horizon. As the specimen tube is tilted, the rouleaux layer 174 sinks to the bottom end of the tube as does the mixture layer 177, while the lighter plasma layer 178 gravitates to the top and comes to rest just under bubble 157. The position of separation boundary 179 can now be measured by comparing the same to a measuring scale 138 on tray 136, or as shown in FIG. 13, a measuring scale 138a on specimen tube 121, to determine the quantity of sedimentation which has occurred during the centrifugation and gravity settling time period.

The entire process, as above described, can be accomplished in less than 5 minutes. Moreover, the quantity of sedimentation which has occurred can be linearly related to Westergren sedimentation units by simply multiplying the sedimentation result in millimeters of fall by a linear multiplier. Using a best fit analysis of the data, extremely high correlation with Westergren data can be obtained using the apparatus of FIG. 7 and a multiplier of 1.88. Correlation using a 1.88 times the measured sedimentation values using the FIG. 7 apparatus and Westergren sedimentation values from specimens from the same patient have been found to have a Pearson correlation coefficient, r, value of approximately 0.99 and $r^2$ value of 0.95, which is an extremely high correlation.

Moreover, and very importantly, the same specimen can be tested again using the present process by simply turning on the mixer after the sedimentation has been measured to re-mix and re-suspend the erythrocytes. The process is then run again until a new sedimentation value is measured. Repeated runs on the same specimen allow an average value to be used. In 20–30 minutes, therefore, the same specimen can be tested three times to produce a highly accurate Westergren sedimentation rate. Achieving three sets of sedimentation data using the Westergren method would require 3 hours, if it could be done, which is not currently possible because the Westergren tube is not sealed, and the specimen would have to be removed, remixed and reinserted into the tube, which would inevitably result in some loss of specimen, requiring the addition of new specimen to make up for the loss. Additionally, such a process is extremely tedious and would require potentially dangerous exposure to contact with the specimen.

FIGS. 15 and 16 illustrate the high correlation of the sedimentation process of the present invention using the apparatus of FIG. 7 with the Westergren process. In FIGS. 15 and 16, the acronym "SSR" stands for "Speedy Sedimentation Rate" and indicates the process of the present invention. The acronym "ESR" stands for "Erythrocyte Sedimentation Rate" and indicates data taken using the Westergren process. FIG. 15 is based upon blood specimens from patients known to have disease or inflammatory conditions. FIG. 16 is based upon blood specimens taken from healthy patients, which specimens were modified, as is well known in the art, by the addition of various amounts of gelatin and/or saline solution to increase the sedimentation rate of the specimen to simulate the sedimentation rates which would occur when a disease or inflammatory condition is present.

In FIGS. 15 and 16, the same blood specimen from a single patient was divided into two sub-specimens and sedimentation was measured with one sub-specimen using the Westergren process and the other sub-specimen using the present process. In the present process, a centrifugation of 400 rpm on a 4 centimeter radius for a time period of 20 seconds and a gravity settling time of 3.5 minutes was used in each case. The SSR data was compared to the ESR data and a multiplier of 1.88 was used in both FIGS. 15 and 16 with the SSR data, based upon a "best fit" analysis of the SSR data to the line of identity.

In FIGS. 15 and 16, therefore, each data point represents two sedimentation rate measurements. Data point 91 on FIG. 15, for example, is a SSR measurement times 1.88 which yielded a sedimentation value of 26 millimeters while the Westergren ESR value for the same patient was 29 millimeters. Data point 92 is a SSR×1.88 value of 48 millimeters and a Westergren ESR of 39 millimeters.

Second Alternative Lag Phase Acceleration Process And Apparatus

A second alternative embodiment of the lag phase acceleration process of the present invention has been found to achieve accelerated blood sedimentation rates which can be linearly related to Westergren rates. FIG. 17 illustrates an apparatus suitable for use with this embodiment of the present process.

A specimen tube 221 is provided which includes an elongated lumen 222 having an elongated member 223 mounted therein. Member 223, however, is a ferromagnetic member, such as a glass or plastic tube 224 having a ferromagnetic material 226 inserted therein and end seals 227. Mounted proximate tube 221 is an electromagnet device 228, and the specimen tube 221 is supported on horizontal surface 229, although stopper 231 provides a slight inclination so that bubble 232 is proximate the stopper end of the specimen tube.

As described above, the specimen 233 is first thoroughly mixed, for example by tilting or rotating tube 221 about a horizontal axis to cause bubble 232 to migrate from one end of the tube to the other. During mixing, if in a magnetized holder, the ferromagnetic rod is fixed to one wall and, if not, ferromagnetic rod 223 is free to translate from side to side inside lumen 222. After mixing tube 221 is placed on surface 229 and the electromagnet energized to pull member 223 to the upper side 235 of lumen 222. The rod is held against upper side 235 for 20 seconds, and it is believed that during that time period rouleaux begin forming in the horn regions between the rod and tube. If this technique were used alone, however, rouleaux formation would still be undesirably slow.

After about 20 seconds, electromagnet 228 is turned off and ferromagnetic rod 223 drops from upper side 235 of the tube lumen to the lower side 240 of lumen 222. The rod motion has a stirring or mixing effect, but it is hypothesized that this motion of rod 223 through specimen 233 is sufficient to create further rouleaux and effectively start the decantation phase.

After 3 to 4 minutes of gravity settling, the specimen can be slowly raised to a vertical position and sedimentation measured. One disadvantage of this alternative embodiment of the present invention is that erythrocytes will remain in suspension in the plasma to a degree giving the plasma a cloudy appearance. This may be the result of the rod's motion through the specimen. Nevertheless, with strong backlighting the plasma/erythrocyte interface can still be located and the sedimentation rate determined. It is believed that location of the interface may be most accurately determined by using automated optical reading apparatus.

Sedimentation rates which linearly correlate to Westergren rates have been obtained in only 4 minutes using this modified embodiment of the invention. As will be appreciated the advantages of shortening the decantation phase by settling across the settling tube are again employed, and syneresis is essentially eliminated.

In describing the preferred embodiments of process and apparatus of the present invention, it will be understood that many of the parameters can be varied within the scope of the present invention. More particularly, gravity settling time periods of 3 to 5 minutes have been found to produce settling rates in a 100 millimeter tube which merely requires multiplication by a factor of 1.75 to 2.25 to produce equivalent Westergren sedimentation rates with an extremely good correlation. As will be appreciated, however, shorter and longer gravity settling times can be employed. Similarly, in the centrifugation embodiment shorter or longer centrifugation times, and higher or lower centrifugation forces, can be employed in combination with differing linear multipliers.

For example, based upon somewhat limited specimen numbers using the centrifugation process to accelerate rouleaux formation, it appears that the best fit multiplier for a 3.0 minute gravity settling period for correlation with Westergren sedimentation rates is a multiplier of 2.12 in a 100 millimeter tube. Similarly, a 4.0 minute gravity settling step appears to correlate with Westergren sedimentation rates using a 1.80 multiplier. The most significant aspect of all three embodiments of the present process and apparatus is not the exact multiplier value, but that the relationship is linear so that a single multiplier can be found for the present process once the various duration parameters are set. It will be appreciated, however, that as the length of the gravity settling step is increased, the erythrocyte packing density can become a factor driving the multiplier into a non-linear range. Thus, the preferred time period for the gravity settling step in a 6 millimeter by 100 millimeter tube with a 4 millimeter rod insert member is between about 2 to about 6 minutes.

Changes in the length and diameter specimen container 21 are also possible and have somewhat less of an effect on the measured sedimentation rates. Since settling occurs when the tube is on its side, the length dimension has very little effect, other than increasing the amount of blood that must be drawn. Diameter effects are greater, both in terms of increasing the specimen size and the distance over which plasma must upwardly migrate as the red cells settle. A lumen height between the rod and tube when the tube is horizontal in the range of about 1 millimeter to about 6 millimeters is believed to be optimum. The volume of blood, however, will increase very rapidly with diameter increases.

With respect to length of time of mixing, certain minimum mixing is required and there is no downside to additional mixing within reasonable time limits such that the cells in the blood specimen are not damaged. There is, however, an overall increase in the time to process a specimen.

The centrifuge time will effect results significantly. As the time is increased, more rouleaux than would be formed during the lag phase will be formed. Settling would accordingly be too rapid or cause the sedimentation multiplication factor to change. A maximum of about 45 seconds of centrifugation can be tolerated, but 20 to 30 seconds at 5–10 g's is preferred. As the spin radius and spin rate are changed, the centrifugal force also will be varied, which will increase or decrease the amount of rouleaux formation.

The rate of the reorientation step to enable measurement is not sensitive in the thin veil embodiment and only slightly more sensitive in the centrifugation and magnetic rod embodiments. If it is too fast, mixing can occur and if it is too slow, additional settling occurs. Reorientation in the range of about 2 to 4 seconds is permissible for the thin veil embodiment and in about 15 to 45 seconds for the centrifugation and magnetic rod embodiments produces substantially the same results, with 20 seconds being preferred.

Once reorientation is accomplished, the sedimentation measurement can be made almost immediately, for example, within 5 seconds. Waiting too long will have some effect on the correlation of data, even though the specimen hematocrit will be high as the specimen will be in the final or syneresis phase. The effect of waiting too long to measure can be significant because of the continual slumping of erythrocytes.

What is claimed is:

1. A container for a liquid specimen comprising:
    an elongated tube defining a lumen extending along a length thereof, said lumen having two side-by-side longitudinally extending lumen portions in septum-free fluid communication with each other over substantially the entire length of said lumen, one of said lumen portions having a sufficiently narrow transverse cross-sectional area to prevent entry of a mixing bubble into said one of said lumen portions while permitting longitudinal flow of a liquid specimen therealong, and a remainder of said lumen portions having a sufficiently wide transverse cross-sectional area over the length thereof to permit movement of a mixing bubble longitudinally in said remainder of said lumen portions while said liquid specimen moves in an opposite direction in said one of said lumen portions to enable mixing of said liquid specimen using said bubble upon tilting of said container.

2. The container for a liquid specimen as defined in claim 1 wherein,
    said one of said lumen portions and said remainder of said lumen portions are formed by a longitudinally extending member mounted in said lumen, said member further being secured to one side of said container and formed extended toward and terminate short of an opposite side of said container over substantially the entire length of said lumen.

3. The container for a liquid specimen as defined in claim 1 wherein,
    said lumen is defined by monolithically formed side walls of said container.

4. The container for a liquid specimen as defined in claim 1 wherein,
    said one lumen portion and said remainder lumen portion are in side-by-side septum-free transverse fluid communication over the entire lengths thereof.

* * * * *